(12) United States Patent
Aoi et al.

(10) Patent No.: US 7,935,939 B2
(45) Date of Patent: May 3, 2011

(54) RADIOTHERAPY APPARATUS CONTROLLER AND RADIATION IRRADIATION METHOD

(75) Inventors: Tatsufumi Aoi, Hiroshima-ken (JP); Shuji Kaneko, Hiroshima-ken (JP); Osamu Shibuya, Hiroshima-ken (JP)

(73) Assignee: Mitsubishi Heavy Industries, Ltd., Tokyo (JP)

( * ) Notice: Subject to any disclaimer, the term of this patent is extended or adjusted under 35 U.S.C. 154(b) by 363 days.

(21) Appl. No.: 12/261,936

(22) Filed: Oct. 30, 2008

(65) Prior Publication Data

US 2009/0189092 A1 Jul. 30, 2009

(30) Foreign Application Priority Data

Jan. 30, 2008 (JP) ................................. 2008-019801

(51) Int. Cl.
*A61B 8/00* (2006.01)
(52) U.S. Cl. ............... 250/491.1; 250/492.1; 250/493.1; 600/414; 600/426; 600/427
(58) Field of Classification Search ............... 250/492.1, 250/491.1, 493.1; 600/414, 426, 427
See application file for complete search history.

(56) References Cited

U.S. PATENT DOCUMENTS

| | | | |
|---|---|---|---|
| 6,144,875 A | 11/2000 | Schweikard et al. | |
| 6,307,914 B1 | 10/2001 | Kunieda et al. | |
| 7,318,805 B2 * | 1/2008 | Schweikard et al. | 600/439 |
| 7,327,865 B2 * | 2/2008 | Fu et al. | 382/128 |
| 7,453,076 B2 * | 11/2008 | Welch et al. | 250/492.3 |
| 7,501,644 B2 * | 3/2009 | Zani et al. | 250/492.21 |
| 7,505,559 B2 * | 3/2009 | Kuduvalli | 378/65 |
| 7,505,617 B2 * | 3/2009 | Fu et al. | 382/128 |
| 7,729,743 B2 * | 6/2010 | Sabczynski et al. | 600/424 |
| 7,773,788 B2 * | 8/2010 | Lu et al. | 382/128 |
| 2006/0002630 A1 * | 1/2006 | Fu et al. | 382/294 |
| 2006/0004281 A1 * | 1/2006 | Saracen | 600/414 |
| 2006/0072821 A1 * | 4/2006 | Wang | 382/173 |
| 2006/0074299 A1 * | 4/2006 | Sayeh | 600/426 |
| 2006/0100509 A1 * | 5/2006 | Wright et al. | 600/426 |
| 2007/0211857 A1 * | 9/2007 | Urano et al. | 378/65 |
| 2007/0284537 A1 * | 12/2007 | Zani et al. | 250/398 |
| 2008/0170663 A1 * | 7/2008 | Urano et al. | 378/65 |
| 2009/0189092 A1 * | 7/2009 | Aoi et al. | 250/492.1 |
| 2009/0257557 A1 * | 10/2009 | Sumanaweera et al. | 378/65 |

FOREIGN PATENT DOCUMENTS

| | | |
|---|---|---|
| JP | 2007-236760 A | 9/2007 |
| JP | 2008-456 A | 1/2008 |
| WO | WO-02/19908 A1 | 3/2002 |

* cited by examiner

*Primary Examiner* — David A Vanore
(74) *Attorney, Agent, or Firm* — Birch, Stewart, Kolasch & Birch, LLP (57) ABSTRACT

A radiotherapy apparatus controller includes: a movement collection section; a sensor control section configured to change a first time interval in which a second sensor measures a position of an irradiation area in the subject, based on the movement information; and an irradiation control section. The movement collection section collects movement information indicating a movement of a subject from a first sensor. The sensor control section changes a first time interval in which a second sensor measures a position of an irradiation area in the subject, based on the movement information. The irradiation control section controls a radiotherapy apparatus such that therapeutic radiation irradiated to the irradiation area is changed based on the position.

32 Claims, 6 Drawing Sheets

RADIOTHERAPY APPARATUS CONTROLLER AND RADIATION IRRADIATION METHOD

INCORPORATION BY REFERENCE

This application is based upon and claims the benefit of priority from Japanese patent application No. 2008-019801 filed on Jan. 30, 2008, the disclosure of which is incorporated herein in its entirety by reference.

BACKGROUND OF THE INVENTION

1. Field of the Invention

The present invention relates to a radiotherapy apparatus controller and a radiation irradiation method, and especially relates to a radiotherapy apparatus controller and a radiation irradiation method used when a patient is treated by irradiating an affected area with a radiation.

2. Description of Related Art

Radiotherapy for treating a patient by irradiating a therapeutic radiation to an affected area (a tumor) is commonly known. A radiation generated by the bremsstrahlung is exemplified as the therapeutic radiation. A method of an irradiation for a wider area than the affected area in consideration of a moving region where the affected area moves, a respiratory-gated radiotherapy (a gated irradiation), and a method of a dynamic tumor-tracking irradiation are known as the radiotherapy. The respiratory-gated radiotherapy is a method for irradiating the therapeutic radiation and stopping the irradiation based on a position of an affected area. The radiotherapy of the dynamic tumor-tracking irradiation is a method for changing an emitting direction or an irradiation field of the therapeutic radiation based on a position of an affected area. The respiratory-gated radiotherapy and the radiotherapy of the dynamic tumor-tracking irradiation are desirable since a dose of the therapeutic radiation irradiated to normal cells other than the affected area is smaller as compared to the radiotherapy of the irradiation for the wider area than the affected area.

In the respiratory-gated radiotherapy and the radiotherapy of the dynamic tumor-tracking irradiation described above, the position of the affected area is required to be consecutively measured. As a measurement method, an X-ray photography method and a MRI (Magnetic Resonance Imaging) method are exemplified. For a target (a lung tumor is exemplified) rapidly moving because of a physiologic movement such as a breath and a pulsating, it is required to shorten a period in which a target position in a body is observed (to increase frequency of the observation) in order to accurately know the target position. The more frequency of the X-ray photography increases, the more a radiation exposure of X-ray for the X-ray photography of a patient increases. Radiotherapy is desired in which a radiation exposure of a patient other than the therapeutic radiation can be reduced.

The law restricts a simultaneous irradiation of the X-ray used for the X-ray photography and the therapeutic radiation to a patient. The MRI needs to operate for a long period of time in order to accurately measure a position of an affected area. The MRI further needs to time-share the observing an affected area by the MRI and the emission of the therapeutic radiation in order to generate a strong magnetic field. For this reason, the more frequency of the observing a position of an affected area increases, the more time for which the therapeutic radiation is irradiated is reduced, and a treatment time will become longer. It is desired to reduce the treatment time of the radiotherapy and to reduce a strain of a patient.

It is desired to more accurately observe a position of an affected area and to reduce frequency of the observing the position of the affected area.

U.S. Pat. No. 6,144,875 discloses a technique for, as for a target moving by a breath, intermittently obtaining a position of the target inside a body by a first sensor and subsequently obtaining a position of the target outside the body by a second sensor, relating the two positions, and estimating the position of the target inside the body based on the position of the target outside the body and irradiating.

U.S. Pat. No. 6,307,914 discloses a technique for, as for a target moving by a breath, performing an X-ray photography at a predetermined frame rate by using two imagers, calculating a three-dimensional position of a marker inside a body base on the images, and irradiating a radiation to the three-dimensional position to treat it.

SUMMARY

An object of the present invention is to provide a radiotherapy apparatus controller and a radiation irradiation method which more reduce frequency of observing a position of an affected area and observe the position of the affected area with more high accuracy.

Another object of the present invention is to provide a radiotherapy apparatus controller and a radiation irradiation method which reduce a radiation exposure by radiation other than the therapeutic radiation.

Another object of the present invention is to provide a radiotherapy apparatus controller and a radiation irradiation method which reduce a treatment time of the radiotherapy.

In a first aspect of the present invention, the present invention provides a radiotherapy apparatus controller including: a movement collection section configured to collect movement information indicating a movement of a subject from a first sensor; a sensor control section configured to change a first time interval in which a second sensor measures a position of an irradiation area in the subject, based on the movement information; and an irradiation control section configured to control a radiotherapy apparatus such that therapeutic radiation irradiated to the irradiation area is changed based on the position.

In the radiotherapy apparatus controller, the second sensor may measure the position based on a transmission radiation transmitted through the subject.

In the radiotherapy apparatus controller, the irradiation control section may control the radiotherapy apparatus such that an irradiation direction of the therapeutic radiation is changed based on the position.

In the radiotherapy apparatus controller, the first time interval may be longer than a second time interval in which the first sensor measures the movement of the subject.

The radiotherapy apparatus controller may further include: a target movement calculation section configured to calculate a rate of change of the position based on the movement information. The sensor control section may change the first time interval based on the rate of change.

The radiotherapy apparatus controller may further include: a correlation calculation section configured to calculate a table correlating a plurality of the movement information with a plurality of the positions based on the movement information and the position. The target movement calculation section may calculate the rate of change based on an estimation position corresponding to the movement information in the plurality of the positions with reference to the table.

The radiotherapy apparatus controller may further include: a target movement calculation section configured to calculate a period of the movement based on the movement information. The sensor control section may change the first time interval based on the period.

In the radiotherapy apparatus controller, the irradiation control section may control the radiotherapy apparatus such that the therapeutic radiation is irradiated in a plurality of time periods in which the second sensor does not measure the position. When a first time period of the plurality of time periods may be longer than a second time period of the plurality of time periods, a first irradiation period in which the therapeutic radiation is irradiated in the first time period may be longer than a second irradiation period in which the therapeutic radiation is irradiated in the second time period.

In a second aspect of the present invention, the present invention provides a radiotherapy system including: the radiotherapy apparatus controller according to any of those as mentioned above; the first sensor; the second sensor; and the radiotherapy apparatus.

In a third aspect of the present invention, the present invention provides a radiation irradiation method including: collecting movement information indicating a movement of a subject from a first sensor; changing a first time interval in which a second sensor measures a position of an irradiation area in the subject, based on the movement information; and controlling a radiotherapy apparatus such that therapeutic radiation irradiated to the irradiation area is changed based on the position.

In the radiation irradiation method, the second sensor may measure the position based on a transmission radiation transmitted through the subject.

In the radiation irradiation method, the controlling step may include: controlling the radiotherapy apparatus such that an irradiation direction of the therapeutic radiation is changed based on the position.

In the radiation irradiation method, the first time interval may be longer than a second time interval in which the first sensor measures the movement of the subject.

The radiation irradiation method may further include: calculating a rate of change of the position based on the movement information. The changing step may include: changing the first time interval based on the rate of change.

The radiation irradiation method may further include: calculating a table correlating a plurality of the movement information with a plurality of the positions based on the movement information and the position. The calculating the rate of change step may include: calculating the rate of change based on an estimation position corresponding to the movement information in the plurality of the positions with reference to the table.

The radiation irradiation method may further include: calculating a period of the movement based on the movement information. The changing step may include: changing the first time interval based on the period.

In the radiation irradiation method, the controlling step may include: controlling the radiotherapy apparatus such that the therapeutic radiation is irradiated in a plurality of time periods in which the second sensor does not measure the position. When a first time period of the plurality of time periods is longer than a second time period of the plurality of time periods, a first irradiation period in which the therapeutic radiation is irradiated in the first time period is longer than a second irradiation period in which the therapeutic radiation is irradiated in the second time period.

In a fourth aspect of the present invention, the present invention provides a computer program product with program code means for carrying out all steps according to any of those as mentioned above if the program runs on a computer.

The computer program product with program code means according to that as mentioned above which are stored on a storage means which can be read by the computer.

A radiotherapy apparatus controller and a radiation irradiation method according to the present invention can reduce a frequency of measuring a position of an irradiated part and measure the position of the irradiated part with high accuracy by lengthening a time interval for measuring the irradiated part when a movement of the irradiated part estimated on the basis of a motion of a subject is slow.

BRIEF DESCRIPTION OF THE DRAWINGS

The above and other objects, advantages and features of the present invention will be more apparent from the following description of certain preferred embodiments taken in conjunction with the accompanying drawings, in which.

DESCRIPTION OF THE PREFERRED EMBODIMENTS

The invention will be now described herein with reference to illustrative embodiments. Those skilled in the art will recognize that many alternative embodiments can be accomplished using the teachings of the present invention and that the invention is not limited to the embodiments illustrated for explanatory purposed.

Figure 1:
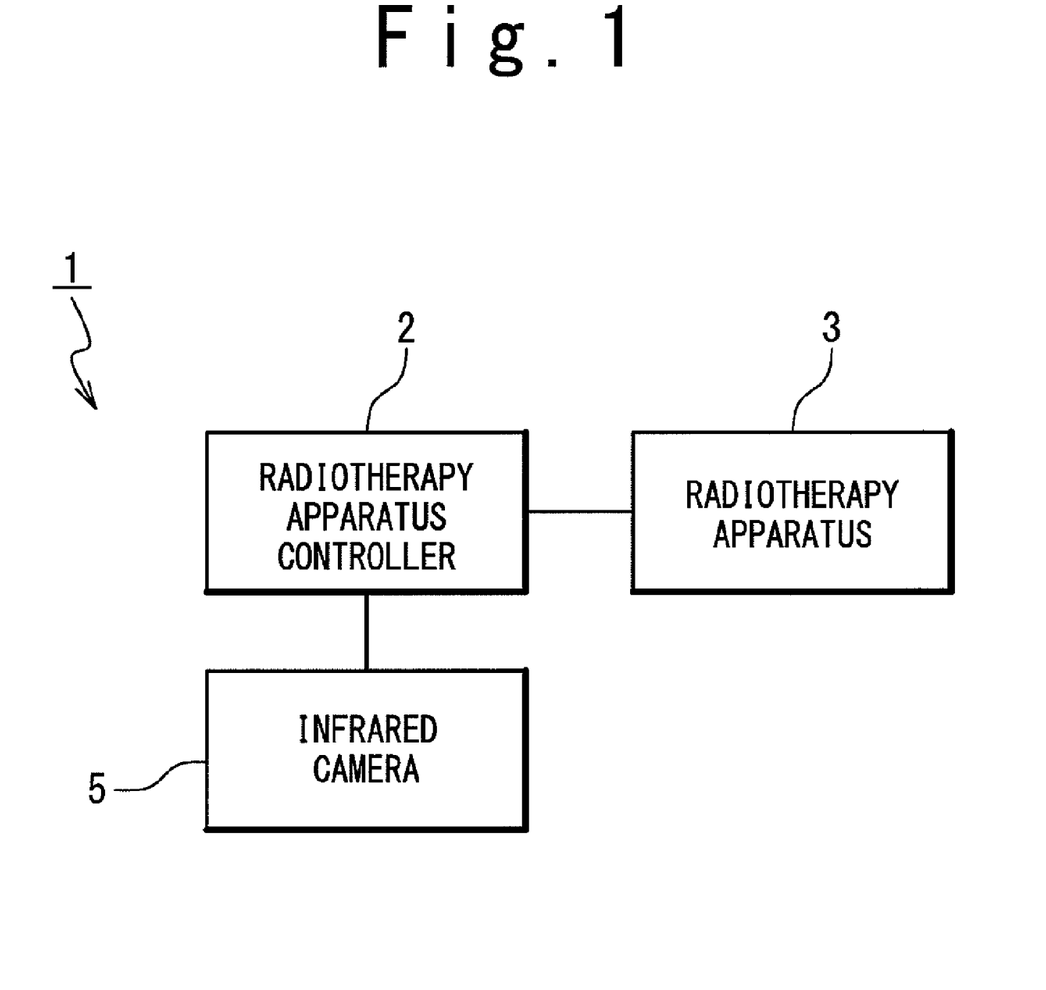
FIG. 1 is a block diagram showing an embodiment of a radiotherapy system according to the present invention.

Referring to drawings, an embodiment of a radiotherapy apparatus controller according to the present invention will be described. The radiotherapy apparatus controller 2 is applied for a radiotherapy system 1 as shown in FIG. 1. The radiotherapy system 1 includes the radiotherapy apparatus controller 2, a radiotherapy apparatus 3, and an infrared camera 5. The radiotherapy apparatus controller 2 is a computer exemplified by a personal computer. The radiotherapy apparatus controller 2 is connected to the radiotherapy apparatus 3 and connected to the infrared camera 5 so as to transfer data bi-directionally.

The infrared camera 5 takes an infrared image of a patient by using a reflection of an infrared ray emitted to the patient and outputs the infrared ray image to the radiotherapy apparatus controller 2.

Figure 2:
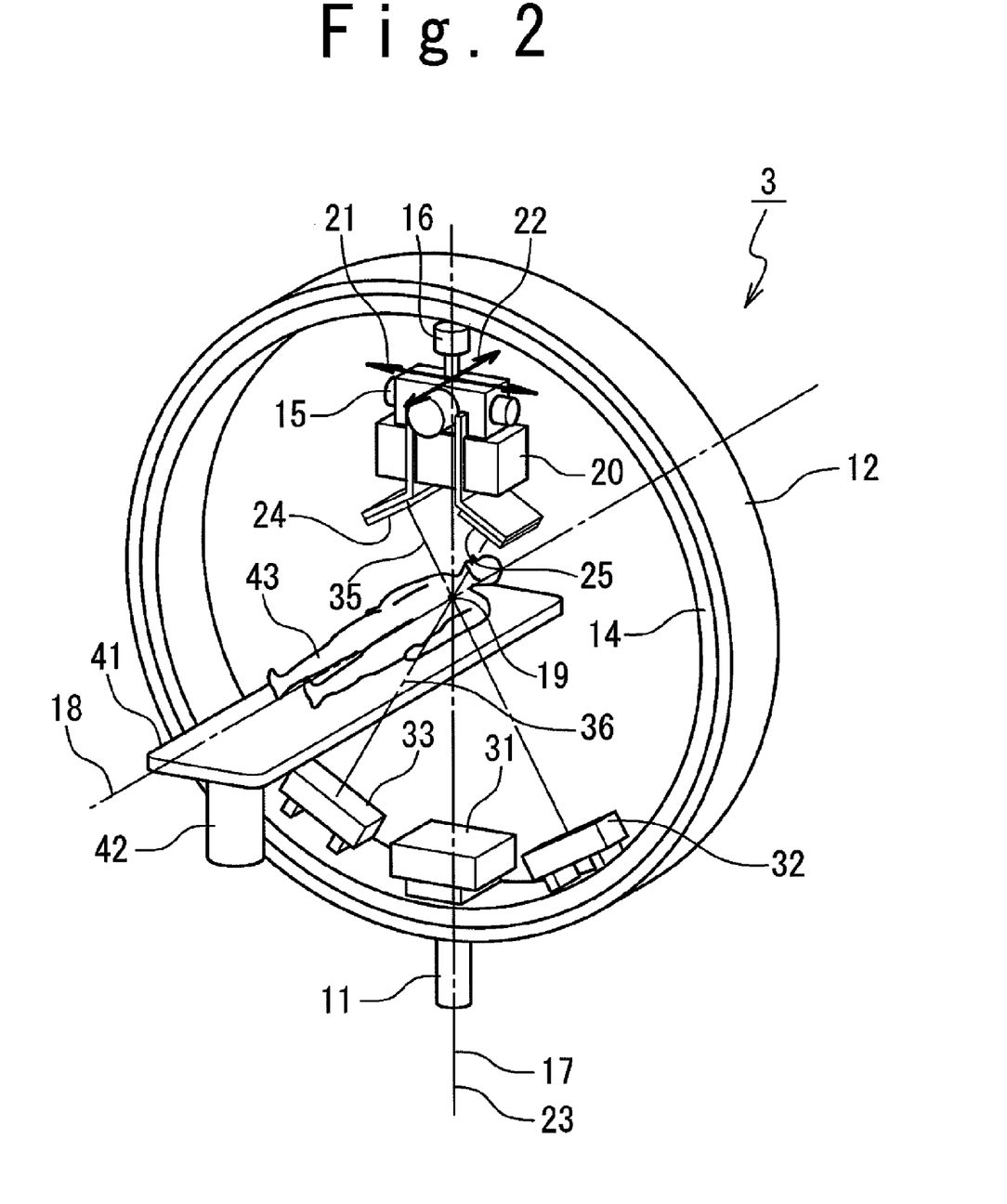
FIG. 2 is a perspective view showing a radiotherapy apparatus.

FIG. 2 shows the radiotherapy apparatus 3. The radiotherapy apparatus 3 includes a revolution drive device 11, an O-ring 12, a traveling gantry 14, a head swing mechanism 15, and a therapeutic radiation irradiating device 16. The revolution drive device 11 rotatably supports the O-ring 12 on a base centering around a rotational axis 17, and rotates the O-ring 12 centering around the rotational axis 17 under a control of the radiotherapy apparatus controller 2. The rotational axis 17 is parallel to a vertical direction. The O-ring 12 is formed in a ring shape centering around a rotational axis 18, and rotatably supports the traveling gantry 14 centering around the rotational axis 18. The rotational axis 18 is perpendicular to the vertical direction, and runs through an isocenter 19 included in the rotational axis 17. The rotational axis 18 is further secured to the O-ring 12, and, for this reason, rotates with the O-ring 12 centering around the rotational axis 17. The traveling gantry 14 is formed in a ring shape centering around the rotational axis 18, and is arranged so as to be a concentric circle with a ring of the O-ring 12. The radiotherapy apparatus 3 further includes a traveling drive device not shown in the figure. The traveling drive device rotates the traveling gantry 14 centering around the rotational axis 18 under control of the radiotherapy apparatus controller 2.

The head swing mechanism 15 is secured inside the ring of the traveling gantry 14, and supports the therapeutic radiation irradiating device 16 on the traveling gantry 14 so that the therapeutic radiation irradiating device 16 can be arranged inside the traveling gantry 14. The head swing mechanism 15 has a pan axis 21 and a tilt axis 22. The tilt axis 22 is secured to the traveling gantry 14, and is parallel to the rotational axis 18 without intersecting with the rotational axis 18. The pan axis 21 is orthogonal to the tilt axis 22. The head swing mechanism 15 rotates the therapeutic radiation irradiating device 16 centering around the pan axis 21 under the control of the radiotherapy apparatus controller 2, and rotates the therapeutic radiation irradiating device 16 centering around the tilt axis 21.

The therapeutic radiation irradiating device 16 radiates a therapeutic radiation 23 under the control of the radiotherapy apparatus controller 2. The therapeutic radiation 23 is radiated almost along a straight line running on the intersection where the pan axis 21 and the tilt axis 22 intersect each other. The therapeutic radiation 23 is formed so as to have a uniform distribution of intensity. The therapeutic radiation irradiating device 16 includes a MLC (multi-leaf collimator) 20. The MLC 20 changes a shape of its irradiation field by shielding a part of the therapeutic radiation 23 under the control of the radiotherapy apparatus controller 2 when the therapeutic radiation 23 is irradiated to the patient.

When the therapeutic radiation irradiating device 16 is once adjusted by the head swing mechanism 15 so as to face the isocenter 19 by being supported on the traveling gantry 14 as described above, the therapeutic radiation 23 constantly and basically passes through the isocenter 19 even when the O-ring 12 is rotated by the revolution drive device 11 or the traveling gantry 14 is rotated by the traveling driving device. That is to say, the therapeutic radiation 23 can be irradiated to the isocenter 19 from an arbitrary direction through the traveling and the rotating.

The radiotherapy apparatus 3 further includes a plurality of imager systems. Concretely, the radiotherapy apparatus 3 includes diagnostic X-ray sources 24 and 25 and sensor arrays 32 and 33. The diagnostic X-ray source 24 is supported by the traveling gantry 14. The diagnostic X-ray source 24 is arranged inside the ring of the traveling gantry 14. The diagnostic X-ray source 24 is arranged at a position where an angle configured by a line segment connecting the isocenter 19 with the diagnostic X-ray source 24 and a line segment connecting the isocenter 19 with the therapeutic radiation irradiating device 16 is an acute angle. The diagnostic X-ray source 24 radiates a diagnostic X-ray 35 to the isocenter 19 under the control of the radio therapy apparatus controller 2. The diagnostic X-ray 35 is a conical corn beam which is radiated from one point included in the diagnostic X-ray source 24 and whose cone point is the one point. The diagnostic X-ray source 25 is supported by the traveling gantry 14. The diagnostic X-ray source 25 is arranged inside the ring of the traveling gantry 14. The diagnostic X-ray source 25 is arranged at a position where an angle configured by a line segment connecting the isocenter 19 with the diagnostic X-ray source 25 and a line segment connecting the isocenter 19 with the therapeutic radiation irradiating device 16 is an acute angle. The diagnostic X-ray source 25 radiates a diagnostic X-ray 36 to the isocenter 19 under the control of the radiotherapy apparatus controller 2. The diagnostic X-ray 36 is a conical corn beam which is radiated from one point included in the diagnostic X-ray source 25 and whose cone point is the one point.

The sensor array 32 is supported by the traveling gantry 14. The sensor array 32 receives the diagnostic X-ray 35 that is radiated by the diagnostic X-ray source 24 and transmits a subject around the isocenter 19, and produces a transmission image of the subject. The sensor array 33 is supported by the traveling gantry 14. The sensor array 33 receives the diagnostic X-ray 36 that is radiated by the diagnostic X-ray source 25 and transmits a subject around the isocenter 19, and produces a transmission image of the subject. As the sensor arrays 32 and 33, a FPD (Flat Panel Detector) and an X-ray II (Image Intensifier) are shown as examples.

According to these imager systems, a transmission image centering around the isocenter 19 can be produced on the basis of image signals obtained by the sensor arrays 32 and 33.

The radiotherapy apparatus 3 further includes a sensor array 31. The sensor array 31 is arranged so that a line segment connecting the sensor array 31 with the therapeutic radiation irradiating device 16 can run on the isocenter 19, and is secured inside the ring of the traveling gantry 14. The sensor array 31 receives the therapeutic radiation 23 radiated by the therapeutic radiation irradiating device 16 and transmitting a subject around the isocenter 19, and produces a transmission image of the subject. As the sensor array 31, the FPD (Flat Panel Detector) and the X-ray II (Image Intensifier) are shown as examples.

The radiotherapy apparatus 3 further includes a couch 41 and a couch driving device 42. The couch 41 is used when a patient 43 to be treated by the radiotherapy system 1 lies down. The couch 41 includes holding fixtures that are not shown in the figure. The holding fixtures fix the patient to the couch 41 so that the patient cannot move. The couch driving device 42 supports the couch 41 on a base, and moves the couch 41 under the control of the radiotherapy apparatus controller 2.

Figure 3:
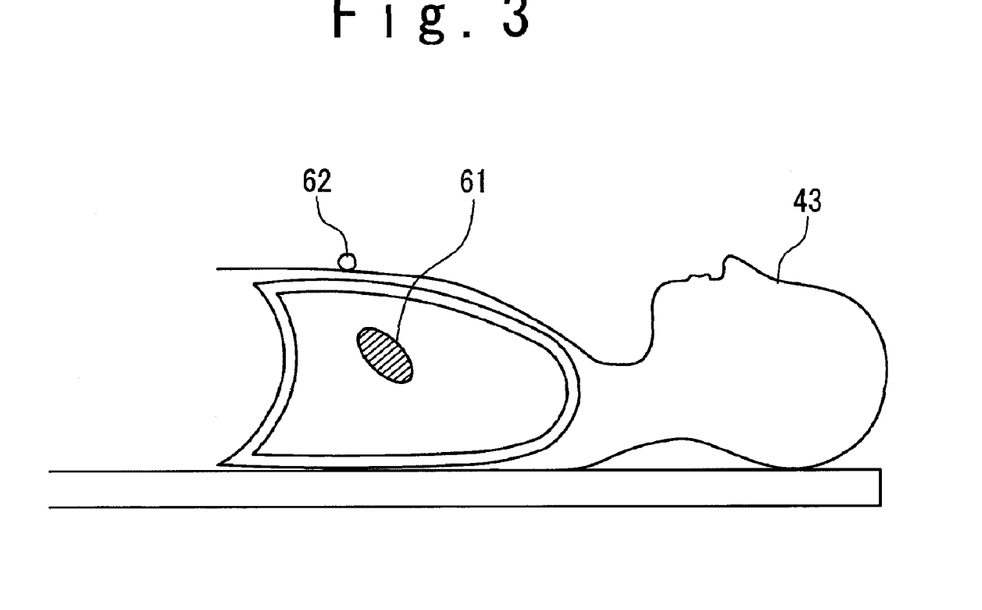
FIG. 3 is a cross sectional view showing a patient.

FIG. 3 shows the patient 43. The patient 43 has a target 61 in his/her body. The target 61 shows an affected part of the patient 43 and shows a portion to be irradiated by the therapeutic radiation 23. A part of the lung is exemplified as the target 61. The patient 43 further has an extracorporeal marker 62 on his/her body. The extracorporeal marker 62 is imaged in an infrared image taken by the infrared camera 5 and is attached on a body surface of the patient 43.

Figure 4:
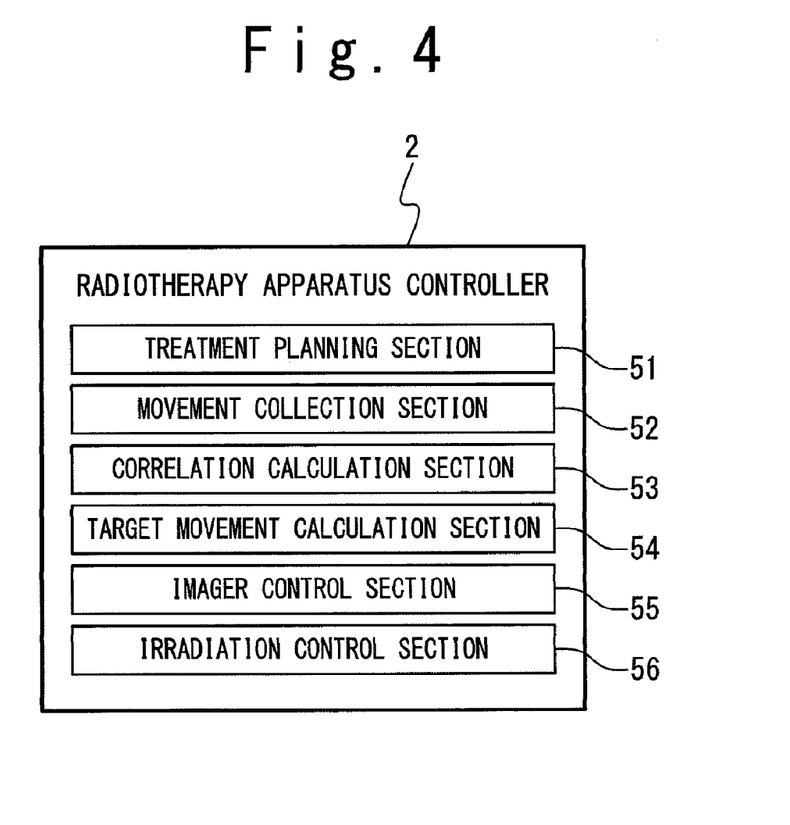
FIG. 4 is a block diagram showing a radiotherapy apparatus controller.

FIG. 4 shows the radiotherapy apparatus controller 2. The radiotherapy apparatus controller 2 is a computer, and includes a CPU, a storage device, an input device, an output device, and an interface those are not shown in the figure. The CPU executes computer programs installed in the radiotherapy apparatus controller 2, and controls the storage device, the input device, and the output device. The storage device stores the computer programs, stores information used by the CPU, and stores data produced by the CPU. The input device outputs information produced by a user's operation to the CPU. As the input device, a keyboard and a mouse are shown as examples. The output device outputs information produced by the CPU so as to be recognized by the user. As the output device, a display is shown as an example. The interface outputs data produced by an outside device connected with the radiotherapy apparatus controller 2 to the CPU, and outputs data produced by the CPU to the outside device. The outside device includes the infrared camera 5, the revolution drive device 11, the head swing mechanism 15, the therapeutic radiation irradiating device 16, the MLC 20, the imager systems (the diagnostic X-ray sources 24 and 25 and the sensor arrays 31, 32, and 33) of the radiotherapy apparatus 3, and the couch driving device 42.

The computer program includes a treatment planning section 51, a movement collection section 52, a correlation calculation section 53, a target movement calculation section 54, an imager control section 55, and an irradiation control section 56.

The treatment planning section 51 shows three dimensional data of the patient 43, which are produced by a computer tomography apparatus not shown in the figure, so that the data can be browsed by a user. The treatment planning section 51 further designs a treatment plan on the basis of data inputted by using the input device. The treatment plan shows the three dimensional data of the target 16 of the patient 43, and shows a combination of an irradiation angle and a radiation dose. The irradiation angle shows a direction of irradiating the therapeutic radiation to the affected area of the patient 43, that is, shows a rotational angle of the O-ring and a rotational angle of the gantry. The rotational angle of the O-ring shows a direction of the O-ring 12 with respect to the base 10. The rotational angle of the gantry shows a direction of the traveling gantry 14 with respect to the O-ring 12. The radiation dose shows a dose of the therapeutic radiation irradiated to the affected area from the respective irradiation angles.

The movement collection section 52 periodically (for example, at every 0.01 sec. to 0.1 sec.) takes infrared images of the extracorporeal marker 62 of the patient 43 by using the infrared camera 5. The movement collection section 52 relates the infrared image to an imaging time and temporarily stores the image in the storage device. The movement collection section 52 further calculates a position of the extracorporeal marker 62 based on the infrared image.

The correlation calculation section 53 calculates a position of the target 61 based on transmission images taken by imager systems of the radiotherapy apparatus 3. Based on the position of the extracorporeal marker 62 calculated by the infrared image taken by the infrared camera 5 at the time near the time when the transmission image was taken, the correlation calculation section 53 further calculates a correlation between the position of the target 61 and the position of the extracorporeal marker 62. The correlation calculation section 53 further produces a table showing the correlation.

The target movement calculation section 54 refers to the table calculated by the correlation calculation section 53 and calculates the position of the target 61 based on the position of the extracorporeal marker 62 calculated by the movement collection section 52. The target movement calculation section 54 further calculates a rate of change of the position of the target 61 based on the calculated position of the target 61 and the imaging time of the infrared image used for the calculation of the position of the extracorporeal marker 62.

The imager control section 55 controls an imager system of the radiotherapy apparatus 3 so that the diagnostic X-rays 35 and 36 can be intermittently emitted and a transmission image of the patient 43 can be taken. The imager control section 55 further calculates a time interval based on the rate of change calculated by the target movement calculation section 54. The time interval is longer than or equal to a time interval when an infrared image is taken by the movement collection section 52, for example, from 1/30 sec. to a few sec. The imager control section 55 further controls the imager systems of the radiotherapy apparatus 3 so that the diagnostic X-rays 35 and 36 can be emitted at the time interval and the transmission image can be taken at the time interval.

The irradiation control section 56 calculates the position of the target 61 based on the transmission image taken by the imager system of the radiotherapy apparatus 3. The irradiation control section 56 drives the therapeutic radiation irradiating device 16 by using the head swing mechanism 15 so that the therapeutic radiation 23 can transmit the calculated position and controls a shape of an irradiation field of the therapeutic radiation 23 by using the MLC 20. The irradiation control section 56 emits the therapeutic radiation 23 by using the therapeutic radiation irradiating device 16 after driving the head swing mechanism 15 and the MLC 20. The longer a period when the diagnostic X-rays 35 and 36 are not emitted is, the longer a period when the therapeutic radiation 23 is emitted becomes. In addition, the irradiation control section 56 can also change a positional relation between the patient 43 and the therapeutic radiation irradiating device 16 by further using the revolution drive device 11, the traveling drive device, or the couch drive device 42 so that the therapeutic radiation 23 can transmit the position of the affected area.

Figure 5:
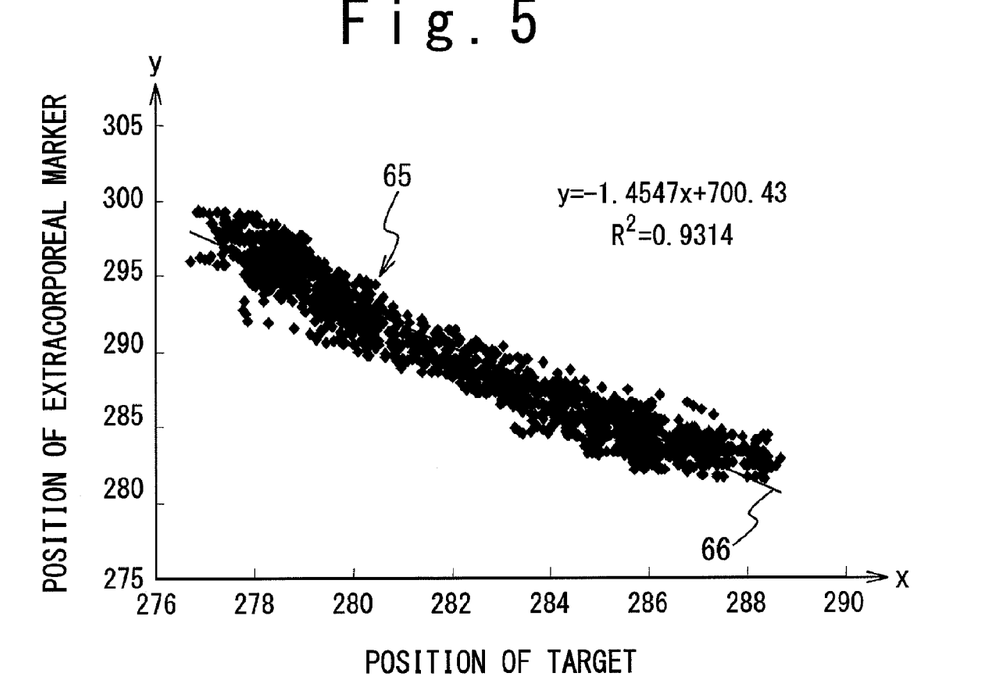
FIG. 5 is a graph showing a correlation chart between a position of an extracorporeal marker and a position of a target and showing a correlation calculated by a correlation calculation section.

FIG. 5 shows an example of a correlation chart between the position of the extracorporeal marker 62 calculated based on the infrared images taken by the infrared camera 5 and the position of the target 61 calculated based on the transmission images taken by the imager systems at the time near the time when the transmission image was taken. The correlation chart 65 shows a strong correlation and shows that the target 61 is synchronized with the extracorporeal marker 62.

FIG. 5 further shows a correlation. The correlation 66 is calculated by the correlation calculation section 53 based on the correlation chart 65, and shows a correlation between the position of the extracorporeal marker 62 and the position of the target 61. Specifically, the correlation calculation section 53 creates the correlation chart 65 within a predetermined time (for example, 10 sec.) based on the infrared images taken by the infrared camera 5 and the transmission images taken by the imager systems of the radiotherapy apparatus 3. The correlation calculation section 53 calculates the correlation 66 based on the correlation chart 65. The correlation calculation section 53 creates a table based on the correlation 66 and temporarily stores the table in the storage device. The table relates a position set of the extracorporeal marker 62 to a position set of the target 61. Concretely, an arbitrary element in the position set of the extracorporeal marker 62 relates to one element in the position set of the target 61.

Figure 6:
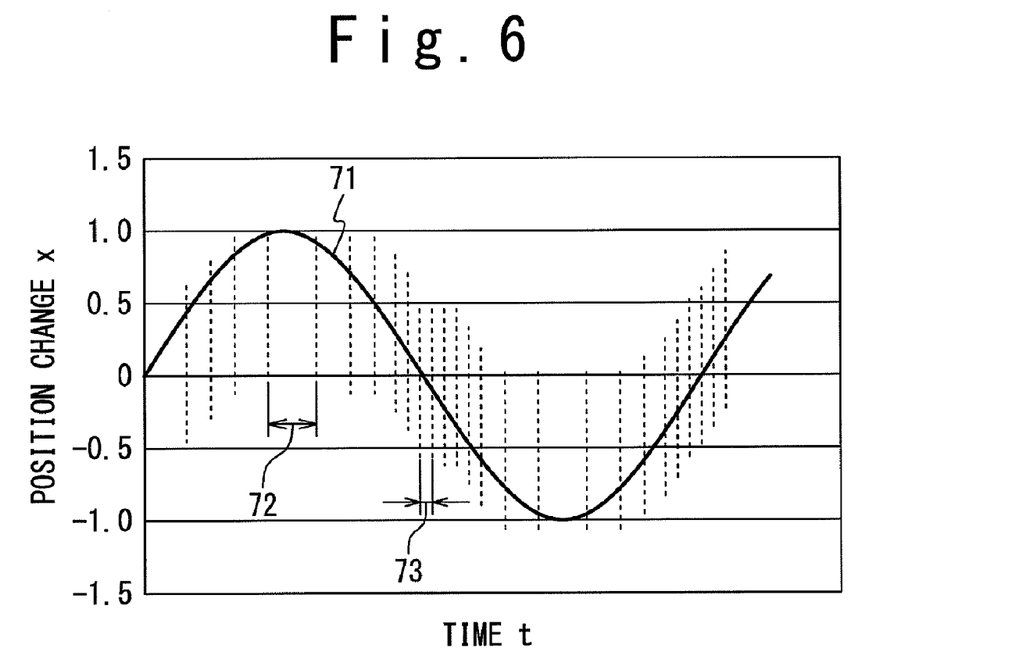
FIG. 6 is a graph showing a position of a target calculated by a target movement calculation section and showing a time interval calculated by an imager control section.

FIG. 6 shows an example of a position change of the target 61 calculated by the target movement calculation section 54. The change 71 shows that a rate of change of the position of the target 61 varies and that the target 61 moves largely periodically. FIG. 6 further shows a timing when the imager systems of the radiotherapy apparatus 3 takes a transmission image (that is, a timing when emitting the diagnostic X-ray 35 or the diagnostic X-ray 36) by a broken line and shows a time interval calculated by the imager control section 55. Furthermore, the time interval is approximately equal to a period when the imager systems of the radiotherapy apparatus 3 do not emit the diagnostic X-rays 35 and 36. FIG. 6 shows that the time interval is not constant and that a time interval 73 calculated at a period when the rate of change of the position of the target 61 is large is small compared to a time interval 72 calculated at a period when the rate of change of the position of the target 61 is small.

On his occasion, the irradiation control section 56 emits the therapeutic radiation 23 at the period when the imager systems of the radiotherapy apparatus 3 do not emit the diagnostic X-rays 35 and 36. The longer the period is, the longer time when the irradiation control section 56 can emit the therapeutic radiation 23 becomes. Specifically, the irradiation control section 56 can emit the therapeutic radiation 23 so that a time when the therapeutic radiation 23 is emitted at the time interval 72 can be longer than the time when the therapeutic radiation 23 is emitted at the time interval 73.

An embodiment of the radiation irradiation method according to the present invention is performed by using the radiotherapy system 1 and includes an operation for creating a treatment plan and an operation for performing the radiotherapy.

In the operation for creating the treatment plan, a user inputs three dimensional data of the patient 43 created by the computer tomography apparatus into the radiotherapy apparatus controller 2 at first. The radiotherapy apparatus controller 2 creates an image showing the affected area of the patient and internal organs around the affected area based on the three dimensional data. The user brows the image by using the radiotherapy apparatus controller 2 and determines the position of the affected area. The user further creates the treatment plan based on the image and inputs the treatment plan into the radiotherapy apparatus controller 2. The treatment plan shows an irradiation angle at which the therapeutic radiation is irradiated to the affected area of the patient and a dose and an aspect of the therapeutic radiation irradiated at the respective irradiation angles.

Figure 7:
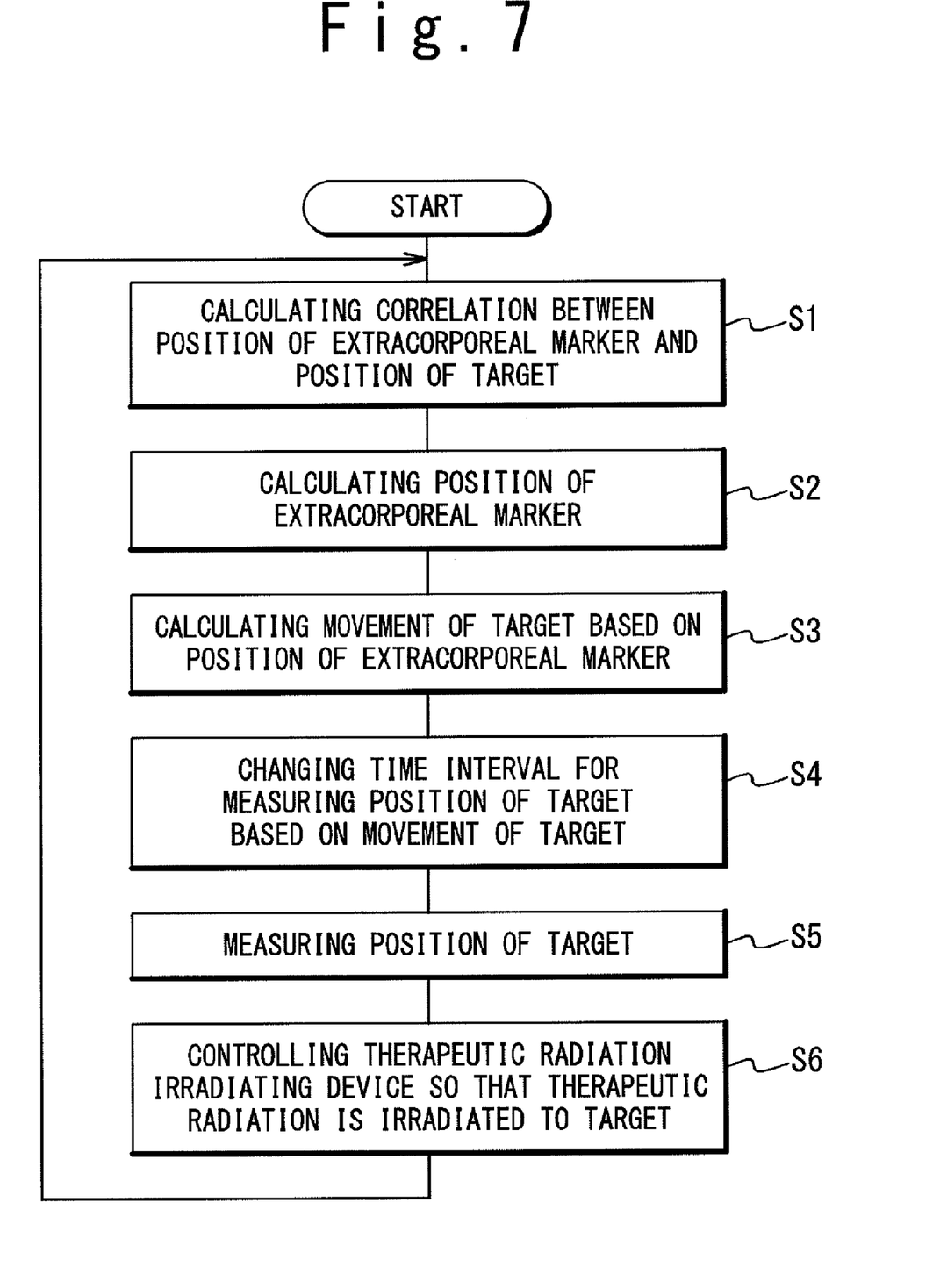
FIG. 7 is a flowchart showing an operation for the radiotherapy.

FIG. 7 shows an operation for performing the radiotherapy. At first, the user fixes the patient 43 on the couch 41 of the radiotherapy apparatus 3 so that the patient 43 can take a position when the treatment plan has been created. The radiotherapy apparatus controller 2 periodically takes the infrared images of the extracorporeal marker 62 by using the infrared camera 5, and periodically takes the transmission images of the target 61 of the patient 43 by using the imager system of the radiotherapy apparatus 3 in parallel with the taking of the infrared images. The radiotherapy apparatus controller 2 creates a table based on the infrared images and the transmission images and temporarily stores the table into the storage device (step S1). The table relates the position set of the extracorporeal marker 62 to the position set of the target 61.

When the radiotherapy starts, the radiotherapy apparatus controller 2 periodically takes infrared images of the extracorporeal marker 62 by using the infrared camera 5 and periodically takes transmission images of the target 61 of the patient 43 by using the imager systems of the radiotherapy apparatus 3. The radiotherapy apparatus controller 2 calculates the position of the extracorporeal marker 62 based on the infrared images (step S2). The radiotherapy apparatus controller 2 calculates the position of the target 61 based on the position of the extracorporeal marker 62 with referring to the table. The radiotherapy apparatus controller 2 further calculates a rate of change of the position of the target 61 based on an imaging time of the infrared images which were used for calculating the position of the extracorporeal marker 62 and the calculated position of the target 61 (step S3).

The radiotherapy apparatus controller 2 calculates the time interval based on the calculated rate of change. The time interval is a value allowing sufficiently accurate measurement of the position of the moving target 61. That is, it shows that the larger an absolute value of the rate of change is, the smaller the value of the time interval is. The radiotherapy apparatus controller 2 controls the imager systems of the radiotherapy apparatus 3 so that the diagnostic X-rays 35 and 36 can be emitted at the time interval and that the transmission images can be taken at the time interval (step S4).

The radiotherapy apparatus controller 2 calculates the position of the target 61 based on the taken transmission images (step S5). The radiotherapy apparatus controller 2 drives the therapeutic radiation irradiating device 16 by using the head swing mechanism 15 and controls the shape of an irradiation field of therapeutic radiation 23 by using the MLC 20 so that the therapeutic radiation 23 can transmit the calculated position. The radiotherapy apparatus controller 2 emits the therapeutic radiation 23 by using the therapeutic radiation irradiating device 16 at a period when the diagnostic X-rays 35 and 36 are not emitted after the head swing mechanism 15 and the MLC 20 are driven (step S6). On this occasion, the radiotherapy apparatus controller 2 further emits the therapeutic radiation 23 for a long time when the length of the time interval is longer.

The radiotherapy apparatus controller 2 repeatedly executes operations of step S1 to step S6 until an irradiation of the therapeutic radiation 23 of a dose indicated in the treatment plan is completed. At step S1 in the repeating, the radiotherapy apparatus controller 2 updates a table based on the infrared images taken at a predetermined period and the transmission images taken at the predetermined period and temporarily stores the table into the storage device. The predetermined period is a period from a time backing a predetermined time period (for example, 10 sec.) from the present time to the present time. That is to say, the infrared images include an infrared image taken as step S2, and the transmission images include the transmission image taken at step S2.

According to these operations, the radiotherapy apparatus controller 2 can accurately measure the position of the moving target 61, which is sufficiently useful for the dynamic tumor-tracking irradiation, and can reduce a frequency of measuring the position of the target 61 by the imager systems of the radiotherapy apparatus 3 in the total of the radiotherapy. The imager systems of the radiotherapy apparatus 3 generally radiate an electromagnetic wave when the diagnostic X-rays 35 and 36 are emitted, and the electromagnetic wave sometimes has harmful effects to other apparatuses. The radiotherapy apparatus controller 2 can reduce the harmful effects to apparatuses included in the radiotherapy apparatus 3 or apparatuses arranged in the vicinity of the radiotherapy apparatus 3 by reducing the frequency of the measurement by the imager systems of the radiotherapy apparatus 3. The radiotherapy apparatus controller 2 can further reduce an amount of electric power consumed by the imager systems of the radiotherapy apparatus 3 in the total of the radiotherapy. The radiotherapy apparatus controller 2 can further reduce a dose of the diagnostic X-rays 35 and 36 irradiated to the patient 43 and reduce an exposure dose of the diagnostic X-rays 35 and 36 irradiated to the patient 43 in the total of the radiotherapy, and can reduce a strain of the patient 43.

Since the longer the time interval when the diagnostic X-rays 35 and 36 are emitted, the longer the time when the therapeutic radiation 23 is emitted, the radiotherapy apparatus controller 2 can increase a dose of the therapeutic radiation 23 emitted per a unit of time and reduce a time for the radiotherapy in the total of the radiotherapy, and can reduce a strain of the patient 43.

Figure 8:
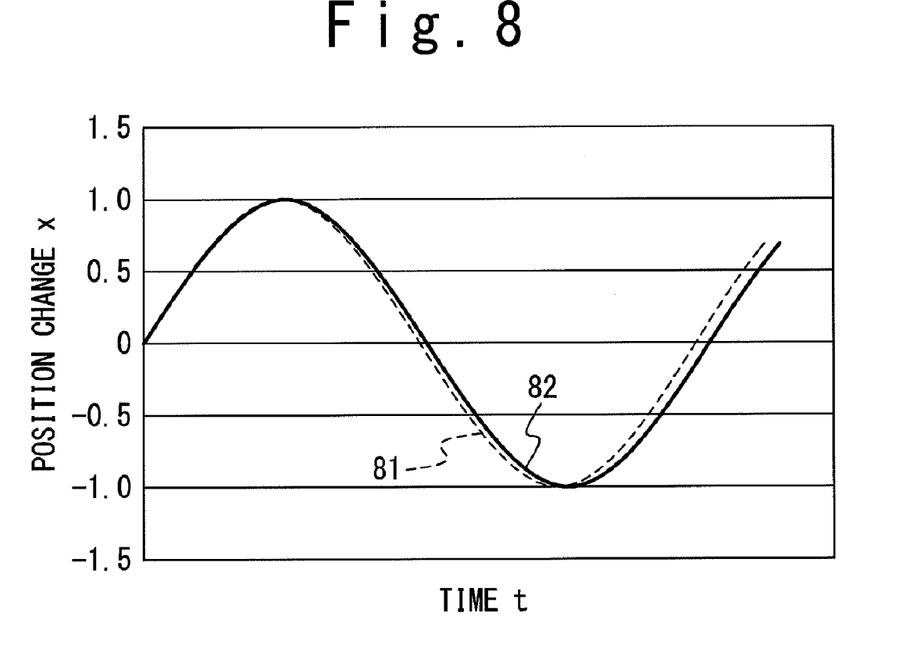
FIG. 8 is a graph showing an example of a position of the target observed immediately before the radiotherapy and a position of the target observed in the middle of the radiotherapy.

FIG. 8 shows an example of a change of the position of the target 61 observed immediately before the radiotherapy. The change 81 shows that the position of the target 61 approximately periodically changes. FIG. 8 further shows an example of a change of the position of the target 61 observed in the middle of the radiotherapy. The change 82 shows that the position of the target 61 approximately periodically changes, and shows that a period of the change is longer than a period of the change 81. As described above, the position of the target 61 approximately periodically changes, however, its period may change.

According to the radiation irradiation method of the present invention, the radiotherapy apparatus controller 2 can measure the position of the moving target 61 at more appropriate time interval and accurately measure the position of the moving target 61, which is sufficiently useful for the dynamic tumor-tracking irradiation.

Figure 9:
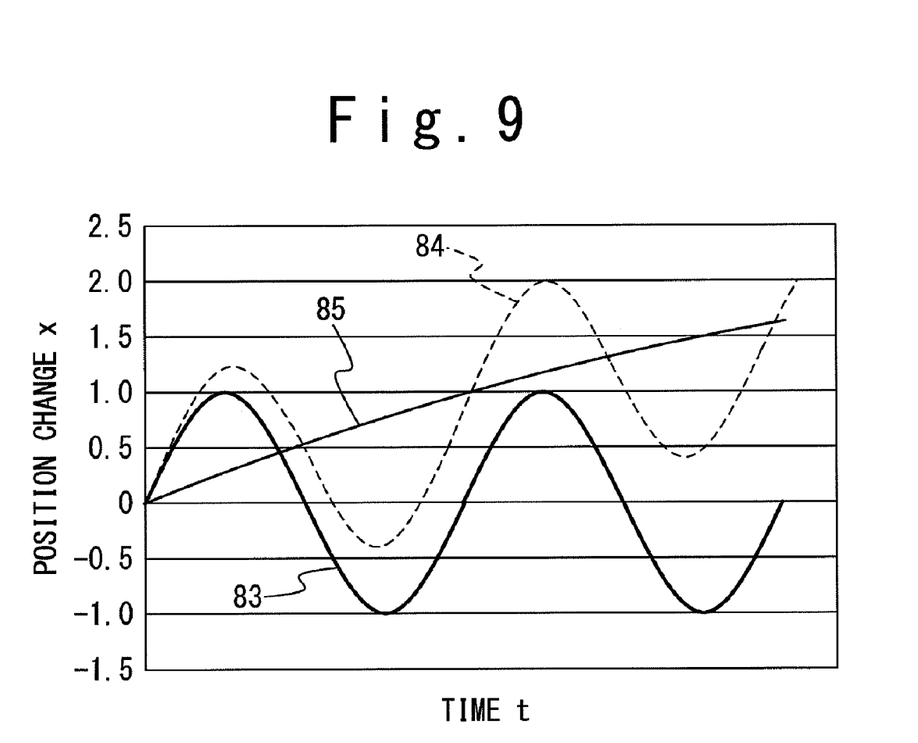
FIG. 9 is a graph showing an example of the position of the target observed immediately before the radiotherapy and the position of the target observed in the middle of the radiotherapy.

FIG. 9 shows another example of the change of the position of the target 61 observed immediately before the radiotherapy. The change 83 shows that the position of the target 61 approximately periodically changes. FIG. 9 further shows another example of the change of the position of the target 61 observed in the middle of the radiotherapy. The change 84 shows that an average position 85 of the target 61 at a predetermined period (time of a natural number multiple of the period) moves as time passes. As described above, the position of the target 61 approximately periodically changes, however, its average position may change as time passes.

According to the radiation irradiation method of the present invention, even in a case where an average position of the target 61 changed, it is possible to measure the position of the moving target 61 at more appropriate time interval and to accurately measure the position of the moving target 61, which is sufficiently useful for the dynamic tumor-tracking irradiation.

In addition, the infrared camera 5 can be replaced by another sensor for measuring movement of the patient 43 exemplified as the breath. A CCD (Charge-Coupled Device) camera, a body surface laser scanner, and a load cell are exemplified as the sensor. The CCD camera takes an image of the extracorporeal marker 62 by using a reflection of a visible ray emitted to the patient 43 and outputs movement information indicating the image to the radiotherapy apparatus controller 2. The body surface laser scanner measures a position and a shape of the body surface of the patient 43 by scanning the body surface with using a laser light emitted to the body surface of the patient 43, and outputs the movement information indicating the position and the shape of the body surface to the radiotherapy apparatus controller 2. The load cell is arranged inside a belt wrapped around an abdomen of the patient 43, measures a pressure applied with being sandwiched by the abdomen and belt, and outputs the movement information indicating the pressure to the radiotherapy apparatus controller 2. On this occasion, the radiotherapy apparatus controller 2 can estimate the movement of the target 61 based on the movement information. That is to say, the radiotherapy apparatus controller 2 can measure the position of the target 61 with sufficiently high accuracy similarly even when the radiotherapy system 1 includes these sensors in place of the infrared camera 52, and can reduce frequency of the measurement of the position of the target 61 by the imager systems of the radiotherapy apparatus 3 in the total of the radiotherapy.

In addition, the imager systems of the radiotherapy apparatus 3 can be replaced by another sensor for measuring a three dimensional position of the target 61. A CT (Computed Tomography) apparatus and an MRI (Magnetic Resonance Imaging) apparatus are exemplified as the sensor.

The CT apparatus takes a plurality of transmission images based on a plurality of X-rays transmitting from a plurality of directions, creates a cross section image of the patient 43 after performing image processing on a plurality of the transmission images in a computer, and calculates the position of the target 61 of the patient 43 by performing image processing on a plurality of the transmission images in the computer. On this occasion, the radiotherapy apparatus controller 2 changes a time interval when the CT apparatus emits the X-ray based on the movement information of the patient 43 in the same way of the imager systems of the radiotherapy apparatus 3.

The MRI apparatus gives a strong magnetostatic field to the patient 43, create an image of three dimensional data of the patient 43 by using a nuclear magnetic resonance, and calculates the position of the target 61 of the patient 43 by performing the image processing on the image. On this occasion, the radiotherapy apparatus controller 2 changes a time interval when the MRI apparatus generates a strong magnetostatic field based on the movement information of the patient 43 in the same way of the imager systems of the radiotherapy apparatus 3.

Consequently, the radiotherapy apparatus controller 2 can measure the position of the target 61 with sufficiently high accuracy in a same way even when the imager systems of the radiotherapy apparatus 3 is replaced by these sensors, and can reduce the frequency of the measurement of the position of the target 61 by the imager systems of the radiotherapy apparatus 3 in the total of the radiotherapy. The radiotherapy apparatus controller 2 can further reduce the harmful effects to apparatuses arranged in a vicinity of the sensor and can reduce an amount of electric power consumed by the sensor.

When the sensor is the CT apparatus, the radiotherapy apparatus controller 2 can further reduce a dose of the X-ray irradiated to the patient 43 by the CT apparatus and can reduce a strain of the patient 43. When the sensor is the MRI apparatus, the radiotherapy apparatus controller 2 can further reduce a dose of the electromagnetic wave irradiated to the patient 43 by the MRI apparatus and can reduce a strain of the patient 43.

In place of the changing the time interval based on the amount of change of the position of the target 61, the radiotherapy apparatus controller 2 may change the time interval based on another value calculated in accordance with a measurement result of the infrared camera 5. The position of the target 61 itself and the movement period of the target are exemplified as the value. It is possible to accurately measure the position of the target 61 similarly even under the control described above, and to reduce frequency of the measurement of the position of the target 61 by the imager systems of the radiotherapy apparatus 3 in the total of the radiotherapy.

Moreover, the technique according to the present invention can be applied to a radiotherapy which performs another radiation irradiation method where the therapeutic radiation 23 changes based on the position of the target 61. A respiratory-gated radiotherapy is exemplified as the radiation irradiation method. On this occasion, the radiotherapy apparatus controller 2 irradiates and stops irradiating the therapeutic radiation 23 based on the measurement result by the imager systems of the radiotherapy apparatus 3. The radiotherapy apparatus controller 2 can accurately measure the position of the target 61 similarly even when applied to the above mentioned radiation irradiation method, and to reduce frequency of the measurement of the position of the target 61 by the imager systems of the radiotherapy apparatus 3 in the total of the radiotherapy.

Although the present invention has been described above in connection with several exemplary embodiments thereof, it would be apparent to those skilled in the art that those exemplary embodiments are provided solely for illustrating the present invention, and should not be relied upon to construe the appended claims in a limiting sense.

What is claimed is:

1. A radiotherapy apparatus controller comprising:
a movement collection section configured to collect movement information indicating a movement of a subject from a first sensor;
a sensor control section configured to change a first time interval in which a second sensor measures a position of an irradiation area in said subject, based on said movement information; and
an irradiation control section configured to control a radiotherapy apparatus such that therapeutic radiation irradiated to said irradiation area is changed based on said position.

2. The radiotherapy apparatus controller according to claim 1, wherein said second sensor measures said position based on a transmission radiation transmitted through said subject.

3. The radiotherapy apparatus controller according to claim 1, wherein said irradiation control section controls said radiotherapy apparatus such that an irradiation direction of said therapeutic radiation is changed based on said position.

4. The radiotherapy apparatus controller according to claim 1, wherein said first time interval is longer than a second time interval in which said first sensor measures said movement of said subject.

5. The radiotherapy apparatus controller according to claim 1, further comprising:
a target movement calculation section configured to calculate a rate of change of said position based on said movement information,
wherein said sensor control section changes said first time interval based on said rate of change.

6. The radiotherapy apparatus controller according to claim 5, further comprising:
a correlation calculation section configured to calculate a table correlating a plurality of said movement information with a plurality of said positions based on said movement information and said position,
wherein said target movement calculation section calculates said rate of change based on an estimation position corresponding to said movement information in said plurality of said positions with reference to said table.

7. The radiotherapy apparatus controller according to claim 1, further comprising:
a target movement calculation section configured to calculate a period of said movement based on said movement information,
where in said sensor control section changes said first time interval based on said period.

8. The radiotherapy apparatus controller according to claim 1, wherein said irradiation control section configured to control said radiotherapy apparatus such that said therapeutic radiation is irradiated in a plurality of time periods in which said second sensor does not measure said position,
wherein when a first time period of said plurality of time periods is longer than a second time period of said plurality of time periods, a first irradiation period in which said therapeutic radiation is irradiated in said first time period is longer than a second irradiation period in which said therapeutic radiation is irradiated in said second time period.

9. A radiotherapy system comprising:
a radiotherapy apparatus controller, wherein said radiotherapy apparatus controller includes:
a movement collection section configured to collect movement information indicating a movement of a subject from a first sensor,
a sensor control section configured to change a first time interval in which a second sensor measures a position of an irradiation area in said subject, based on said movement information, and
an irradiation control section configured to control a radiotherapy apparatus such that therapeutic radiation irradiated to said irradiation area is changed based on said position;
said first sensor;
said second sensor; and
said radiotherapy apparatus.

10. The radiotherapy system according to claim 9, wherein said second sensor measures said position based on a transmission radiation transmitted through said subject.

11. The radiotherapy system according to claim 9, wherein said irradiation control section controls said radiotherapy apparatus such that an irradiation direction of said therapeutic radiation is changed based on said position.

12. The radiotherapy system according to claim 9, wherein said first time interval is longer than a second time interval in which said first sensor measures said movement of said subject.

13. The radiotherapy system according to claim 9, wherein said radiotherapy apparatus controller further includes:
a target movement calculation section configured to calculate a rate of change of said position based on said movement information,
wherein said sensor control section changes said first time interval based on said rate of change.

14. The radio therapy system according to claim 13, wherein said radiotherapy apparatus controller further includes:
a correlation calculation section configured to calculate a table correlating a plurality of said movement information with a plurality of said positions based on said movement information and said position,
wherein said target movement calculation section calculates said rate of change based on an estimation position corresponding to said movement information in said plurality of said positions with reference to said table.

15. The radiotherapy system according to claim 9, wherein said radiotherapy apparatus controller further includes:
a target movement calculation section configured to calculate a period of said movement based on said movement information,
wherein said sensor control section changes said first time interval based on said period.

16. The radiotherapy system according to claim 9, wherein said irradiation control section configured to control said radiotherapy apparatus such that said therapeutic radiation is irradiated in a plurality of time periods in which said second sensor does not measure said position,
wherein when a first time period of said plurality of time periods is longer than a second time period of said plurality of time periods, a first irradiation period in which said therapeutic radiation is irradiated in said first time period is longer than a second irradiation period in which said therapeutic radiation is irradiated in said second time period.

17. A radiation irradiation method comprising:
collecting movement information indicating a movement of a subject from a first sensor;
changing a first time interval in which a second sensor measures a position of an irradiation area in said subject, based on said movement information; and
controlling a radiotherapy apparatus such that therapeutic radiation irradiated to said irradiation area is changed based on said position.

18. The radiation irradiation method according to claim 17, wherein said second sensor measures said position based on a transmission radiation transmitted through said subject.

19. The radiation irradiation method according to claim 17, wherein said controlling step includes:
controlling said radiotherapy apparatus such that an irradiation direction of said therapeutic radiation is changed based on said position.

20. The radiation irradiation method according to claim 17, wherein said first time interval is longer than a second time interval in which said first sensor measures said movement of said subject.

21. The radiation irradiation method according to claim 17, further comprising:
calculating a rate of change of said position based on said movement information,
wherein said changing step includes:
changing said first time interval based on said rate of change.

22. The radiation irradiation method according to claim 21, further comprising:
calculating a table correlating a plurality of said movement information with a plurality of said positions based on said movement information and said position,
wherein said calculating said rate of change step includes:
calculating said rate of change based on an estimation position corresponding to said movement information in said plurality of said positions with reference to said table.

23. The radiation irradiation method according to claim 17, further comprising:
calculating a period of said movement based on said movement information,
wherein said changing step includes:
changing said first time interval based on said period.

24. The radiation irradiation method according to claim 17, wherein said controlling step includes:
controlling said radiotherapy apparatus such that said therapeutic radiation is irradiated in a plurality of time periods in which said second sensor does not measure said position,
wherein when a first time period of said plurality of time periods is longer than a second time period of said plurality of time periods, a first irradiation period in which said therapeutic radiation is irradiated in said first time period is longer than a second irradiation period in which said therapeutic radiation is irradiated in said second time period.

25. A computer-readable medium comprising code that, when executed, causes a computer to perform the following:
collecting movement information indicating a movement of a subject from a first sensor;
changing a first time interval in which a second sensor measures a position of an irradiation area in said subject, based on said movement information; and
controlling a radiotherapy apparatus such that therapeutic radiation irradiated to said irradiation area is changed based on said position.

26. The computer-readable medium according to claim 25, wherein said second sensor measures said position based on a transmission radiation transmitted through said subject.

27. The computer-readable medium according to claim 25, wherein said controlling step includes:
controlling said radiotherapy apparatus such that an irradiation direction of said therapeutic radiation is changed based on said position.

28. The computer-readable medium according to claim 25, wherein said first time interval is longer than a second time interval in which said first sensor measures said movement of said subject.

29. The computer-readable medium according to claim 25, further comprising:
calculating a rate of change of said position based on said movement information,
wherein said changing step includes:
changing said first time interval based on said rate of change.

30. The computer-readable medium according to claim 29, further comprising:
calculating a table correlating a plurality of said movement information with a plurality of said positions based on said movement information and said position,
wherein said calculating said rate of change step includes:
calculating said rate of change based on an estimation position corresponding to said movement information in said plurality of said positions with reference to said table.

31. The computer-readable medium according to claim 25, further comprising:
calculating a period of said movement based on said movement information,
wherein said changing step includes:
changing said first time interval based on said period.

32. The computer-readable medium according to claim 25, wherein said controlling step includes:
controlling said radiotherapy apparatus such that said therapeutic radiation is irradiated in a plurality of time periods in which said second sensor does not measure said position,
wherein when a first time period of said plurality of time periods is longer than a second time period of said plurality of time periods, a first irradiation period in which said therapeutic radiation is irradiated in said first time period is longer than a second irradiation period in which said therapeutic radiation is irradiated in said second time period.

* * * * *